(12) United States Patent
Church et al.

(10) Patent No.: US 10,149,953 B2
(45) Date of Patent: Dec. 11, 2018

(54) BREATH INDICATOR

(75) Inventors: Jonathan Mark Church, Manukau (NZ); Simon Boulton, Auckland (NZ); David Robert Kemps, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 677 days.

(21) Appl. No.: 13/820,018

(22) PCT Filed: Aug. 31, 2011

(86) PCT No.: PCT/NZ2011/000174
§ 371 (c)(1),
(2), (4) Date: May 9, 2013

(87) PCT Pub. No.: WO2012/030232
PCT Pub. Date: Mar. 8, 2012

(65) Prior Publication Data
US 2013/0220326 A1    Aug. 29, 2013

Related U.S. Application Data

(60) Provisional application No. 61/379,989, filed on Sep. 3, 2010.

(51) Int. Cl.
*A61M 16/00* (2006.01)
*A61B 5/083* (2006.01)
(Continued)

(52) U.S. Cl.
CPC ....... *A61M 16/0057* (2013.01); *A61B 5/0836* (2013.01); *A61B 5/4836* (2013.01);
(Continued)

(58) Field of Classification Search
CPC ... A61B 5/0836; A61B 5/682; A61B 2503/04; A61B 5/745; A61B 5/4836; A61B 5/097;
(Continued)

(56) References Cited

U.S. PATENT DOCUMENTS 4,346,584 A * 8/1982 Boehringer .......... A61B 5/0836
600/532
4,790,327 A * 12/1988 Despotis ........... A61M 16/0488
128/205.23
(Continued)

FOREIGN PATENT DOCUMENTS

EP          0257916 A1   3/1988
WO   WO 1989/007957 A1   9/1989
WO   WO 1997/033641 A1   9/1997

OTHER PUBLICATIONS

International Search Report and Written Opinion; dated Dec. 8, 2011; 10 pages.
(Continued)

*Primary Examiner* — Gregory Anderson
*Assistant Examiner* — Elliot S Ruddie
(74) *Attorney, Agent, or Firm* — Knobbe, Martens, Olson & Bear, LLP

(57) ABSTRACT

This invention relates to a breath indicator that is receivable by a part of a breathing assistance apparatus that supplies gas to a patient. The indicator comprises an elongate body having a gas sampling end and an attachment end. The attachment end is adapted to attach to a part of a breathing assistance apparatus and for locating the gas sampling end. The gas sampling end is to be located in a region where gas from the patient is to be exhaled. The gas sampling end being in communication with a sensor comprising a detector material changeable between a first visual indicator state relating to an inhalation phase of the patient, and a second visual indicator state relating to an exhalation phase of the patient. The detector material is capable of changing between the visual indicator states at a sufficient rate to substantially correspond with the inhalation and exhalation phases of the patient.

18 Claims, 6 Drawing Sheets

(51) Int. Cl.
*A61B 5/00* (2006.01)
*A61M 16/08* (2006.01)
*A61M 16/20* (2006.01)
*A61M 16/04* (2006.01)
*A61M 16/06* (2006.01)
*G01N 31/22* (2006.01)
*A61M 16/16* (2006.01)

(52) U.S. Cl.
CPC ............ *A61M 16/00* (2013.01); *A61M 16/04* (2013.01); *A61M 16/0666* (2013.01); *A61M 16/0816* (2013.01); *A61M 16/0833* (2014.02); *A61M 16/0875* (2013.01); *A61M 16/20* (2013.01); *A61B 5/682* (2013.01); *A61B 5/745* (2013.01); *A61B 2503/04* (2013.01); *A61M 16/0463* (2013.01); *A61M 16/06* (2013.01); *A61M 16/161* (2014.02); *A61M 16/209* (2014.02); *A61M 2016/0413* (2013.01); *A61M 2205/0227* (2013.01); *A61M 2205/3368* (2013.01); *A61M 2205/583* (2013.01); *A61M 2205/584* (2013.01); *A61M 2230/432* (2013.01); *A61M 2240/00* (2013.01); *G01N 31/22* (2013.01)

(58) Field of Classification Search
CPC .......... A61M 2016/0413; A61M 16/06; A61M 16/0816; A61M 16/20; A61M 2205/583; A61M 2205/584; A61M 2230/432; A61M 16/0057; A61M 16/04; A61M 16/0666; A61M 16/0875; A61M 16/0833; A61M 16/085; A61M 16/00; A61M 16/0051; A61M 16/0402; A61M 16/0411; G01N 31/22; G01N 31/223
USPC ............ 128/202.22, 204.18, 204.22, 204.23, 128/205.28, 208.23; 422/83, 84, 85, 86, 422/87, 400, 401, 420
See application file for complete search history.

(56) References Cited

U.S. PATENT DOCUMENTS

| | | | |
|---|---|---|---|
| 4,879,999 A * | 11/1989 | Leiman | A61M 16/04 128/202.22 |
| 4,945,918 A | 8/1990 | Abernathy | |
| 5,857,460 A | 1/1999 | Popitz | |
| 6,058,933 A * | 5/2000 | Good | A61M 16/0078 128/202.28 |
| 6,502,573 B1 * | 1/2003 | Ratner | A61M 16/208 128/202.22 |
| 6,584,974 B1 * | 7/2003 | Ratner | A61M 1/0072 128/205.23 |
| 6,709,403 B1 * | 3/2004 | Ratner | A61M 16/0051 422/84 |
| 6,929,008 B2 * | 8/2005 | Geist | A61M 16/08 128/202.22 |
| 7,246,622 B2 | 7/2007 | Geist | |
| 2004/0040559 A1 | 3/2004 | Moody et al. | |
| 2008/0078394 A1 * | 4/2008 | Ostrowski | B01J 20/10 128/205.13 |
| 2010/0305464 A1 | 12/2010 | Ratner | |

OTHER PUBLICATIONS

European Search Report; Application No. 11822183.7, dated Jun. 15, 2015; 7 pages.
Australian Examination Report; Application No. 2011296642, dated Jun. 5, 2015; 3 pages.
Examination Report from Australian Patent Application No. 2011296642, dated May 19, 2016, in 3 pages.
Examination Report from Australian Patent Application No. 2016219709, dated May 18, 2017, in 3 pages.
Examination Report from Canadian Patent Application No. 2809932, dated May 15, 2017, in 4 pages.
Extended Search Report from European Patent Application No. 17169097.7, dated Oct. 11, 2017, in 8 pages.
Examination Report from Australian Patent Application No. 2016219709, dated Mar. 6, 2018, in 2 pages.

* cited by examiner

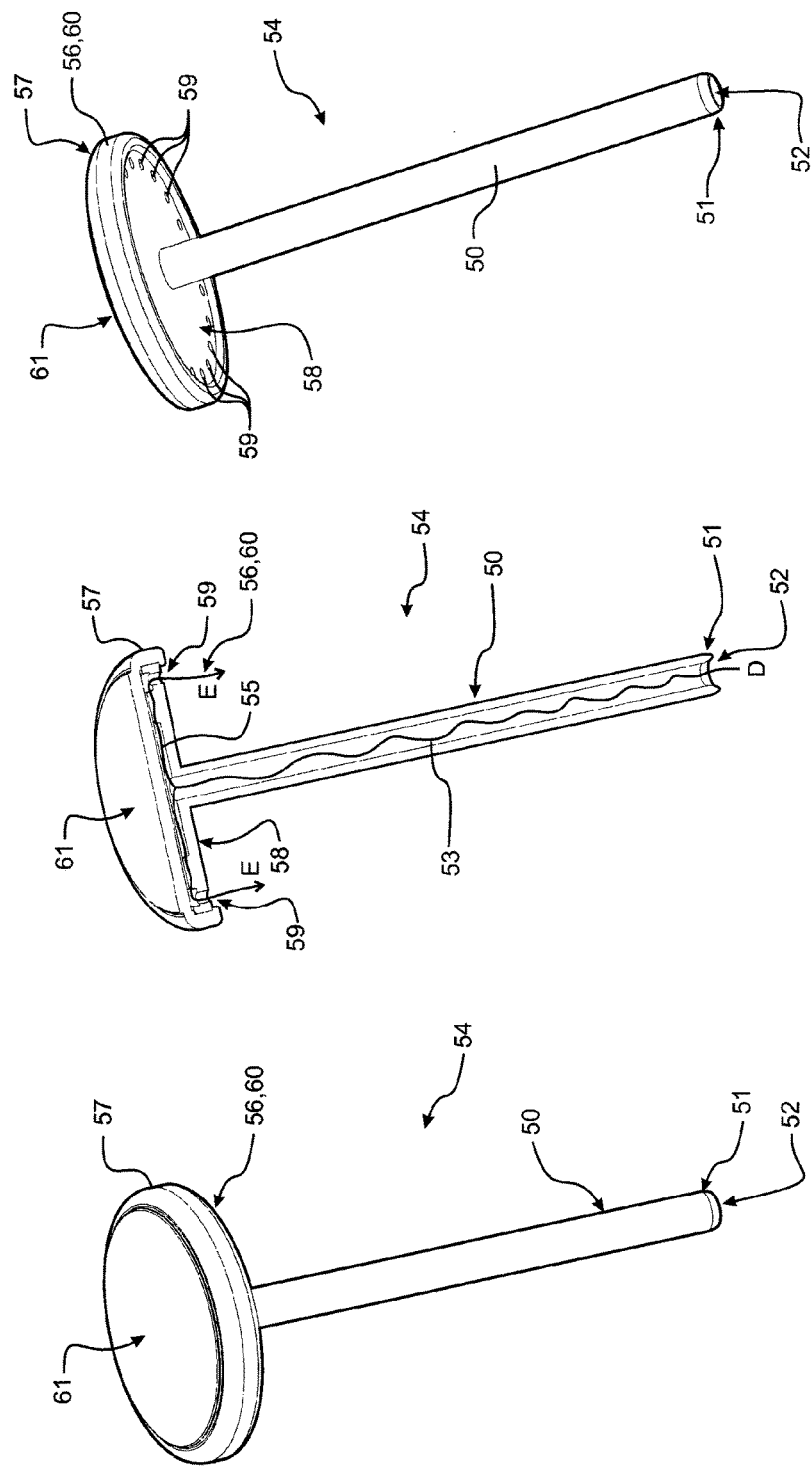

BREATH INDICATOR

INCORPORATION BY REFERENCE TO ANY PRIORITY APPLICATIONS

Any and all applications for which a foreign or domestic priority claim is identified in the Application Data Sheet as filed with the present application, are hereby incorporated by reference under 37 CFR 1.57.

BACKGROUND OF THE INVENTION

Field of the Invention

The present invention relates to a breath indicator for detecting inhalation or exhalation for use in conjunction with or as part of a breathing assistance apparatus which is used for resuscitating and/or supplying gases to an infant.

Description of the Related Art

It is known to apply Positive End Expiratory Pressure (PEEP) and controlled Peak Inspiratory Pressure (PIP) during respiration, resuscitation or assisted respiration (ventilation) for patients, such as neonates or infants who require breathing assistance. In applying PEEP, the patient, such as an infant's upper airway and lungs are held open by the applied pressure. An example of an apparatus suitable for this is disclosed in US2004/0040559.

It is important for a medical professional to be able to establish and verify the breathing of the infant. When undergoing assisted ventilation or respiration, the neonatal infant will receive a continuous flow of gases to their airway. These gases will either be atmospheric, atmospheric with supplementary added oxygen, or (rarely) pure oxygen. When the patient infant exhales against the continuous flow of gases, they will breathe out gases that have a higher concentration of $CO_2$ than those which enter their lungs.

It is known to use $CO_2$ detectors with adult ventilation systems and as part of breathing masks. U.S. Pat. No. 4,945,918 discloses using a $CO_2$ detector with a ventilation system to detect the patient's circulatory status. U.S. Pat. No. 5,857,460 discloses a mask with a gas sensor positioned on the mask.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

It is an object of the present invention to provide a breath indicator for use with a breathing assistance apparatus, or a breathing assistance apparatus with a breath indicator that will at least provide the healthcare industry with a useful choice.

In a first aspect the invention can be said to broadly consist of breath indicator receivable by a part of a breathing assistance apparatus that supplies gas to a patient, the indicator comprising: an elongate body having a gas sampling end and an attachment end, the attachment end adapted to attach to a part of a breathing assistance apparatus and for locating the gas sampling end, and the gas sampling end to be located in a region where gas from the patient is to be exhaled, the gas sampling end being in communication with a sensor comprising a detector material changeable between a first visual indicator state relating to an inhalation phase of the patient, and a second visual indicator state relating to an exhalation phase of the patient, and wherein the detector material is capable of changing between the visual indicator states at a sufficient rate to substantially correspond with the inhalation and exhalation phases of the patient.

Preferably the detecting material is $CO_2$ detecting material.

Preferably the sensor comprises $CO_2$ detecting material.

Preferably the detecting material changes from a first visual indicator state to a second indicator state when exposed to gas having $CO_2$ concentration greater than that normally found in atmospheric air.

Preferably the detecting material changes from a second visual indicator state to a first indicator state when exposed to gas having $CO_2$ concentration the same or substantially similar to those normally found in atmospheric air.

Preferably the detecting material changes from the first visual indicator state (a first colour) to a second visual indicator state (a second colour) when exposed to gas having a concentration by volume of at least about 5% or more $CO_2$.

Preferably the visual indicator state of the detecting material can be optically or visually observed by a user of a breathing assistance apparatus for a patient.

Preferably in-use, end-tidal or breath-by-breath $CO_2$ present within gas exhaled by a patient is optically or visually observable by a user by change in visual indictor state of the detecting material.

Preferably at least a part of the attachment end remains external of a part of a breathing assistance apparatus to which the breath indicator is attached.

Preferably the attachment end is provided substantially perpendicular to the elongate body.

Preferably the attachment end is disk-shaped.

Preferably the attachment end is formed as a handle portion including a handle flange extending outwards perpendicularly from the end of the attachment end.

Preferably said breath indicator further comprises a stopping flange located partway along said elongate body and extending substantially perpendicularly from said body, said flange located between said attachment end and said sampling end.

Preferably the breath indicator is receivable by a patient interface.

Preferably the patient interface comprises any one or combination of the following: a face mask, an oral mask, an oronasal mask, a nasal mask, one or a pair of nasal prongs, an endotracheal tube, a T-piece resuscitator apparatus, gas flow regulator or gas pressure regulator associated with any one or more of these.

Preferably the breath indicator is receivable by a face mask.

Preferably the breath indicator is receivable by a T-piece breathing assistance apparatus.

Preferably the exterior surface of the elongate body is substantially smooth, or otherwise shaped, such that, in-use the elongate body does not increase the resistance to flow of gas through a part of a breathing assistance apparatus to which the indicator is attached.

Preferably the elongate body has an outer diameter of about 1 mm to about 5 mm, and a length of about 30 mm to about 60 mm.

Preferably the gas sampling end of the elongate body comprises a gas inlet, the inlet being in fluid communication with the sensor via a passageway.

Preferably a pressure difference exists between the gas sampling end and the attachment end when in use.

Preferably the sensor comprising the detecting material is provided in-line with the passageway.

Preferably the passageway extends from the gas sampling end of the elongate body to the sensor.

Preferably the passageway provides for a gas flow path extending from the breath indicator gas inlet to one or more breath indicator gas outlets, the outlets in fluid communication with the surrounding atmosphere external of the resuscitation system, the sensor positionable for contact with the gas flow path through the passageway.

Preferably the sensor with detecting material is located in a region adjacent the attachment end, and wherein the attachment end, or at least a part of the attachment end, is formed of a visually transparent material allowing a user to visually detect changes between the first and second visual indicator states of the detector material.

Preferably the attachment end houses the sensor.

Preferably the attachment end comprises a housing locating the sensor.

Preferably at least a part of the attachment end (or housing) is formed of a visually transparent material, such that in-use, a user is able to visually detect changes between the first and second visual indicator states of the detector material.

Preferably the elongate body has a length sufficient to allow the gas sampling end to be located in a region where gas from the patient is to be exhaled, and where the attachment end is located in a position attached to a part of a breathing assistance apparatus.

Preferably the sampling end and sensor are substantially adjacent, or are the same part of region of the elongate body.

Preferably the sensor is formed as a hollow section of the sampling end, the hollow section filled with an indicator dye, the wall or shell of said hollow section having pores to allow gases to pass through the wall or shell and contact the indicator dye, the wall or shell substantially clear or translucent to allow a user to view the colour of the dye through the wall or shell.

Preferably the detecting material is a layer of indicator dye applied to the outside surface of the sampling end, the detecting material applied to at least part of the area or region of the elongate body near the sampling end.

Preferably the sampling end is at least partly (preferably wholly) formed from detecting material and attached or connected to the remainder of the elongate body.

Preferably said detecting material is applied to the entire area of said elongate body.

Preferably said detecting material is a layer of material infused with a CO2 detecting material and applied to the outside surface of the sampling end.

Preferably the elongate body includes a plurality of apertures.

Preferably the apertures are arranged in a substantially honeycomb pattern.

Preferably the apertures are circular, oval, square, rectangular or triangular-shaped.

Preferably the apertures are positioned adjacent to the attachment end of the elongate body.

Preferably the apertures are positioned about 1 mm to about 15 mm along the elongate body from the attachment end.

Preferably the apertures are positioned about 7 mm to about 10 mm along the elongate body from the attachment end.

Preferably the apertures are positioned adjacent to the sensor.

Preferably the apertures are positioned about 1 mm to about 15 mm along the elongate body from the sampling end.

Preferably the apertures are positioned about 7 mm to about 10 mm along the elongate body from the sampling end.

Preferably in-use the elongate body is inserted into a breathing assistance apparatus that supplies gas to a patient, such that the sampling end is located proximate to the mouth and nose of the patient and such that the apertures are positioned in a flow of gas from an inlet to the breathing assistance apparatus, and wherein, in-use, gas from the inlet flow through the apertures generates suction in the breathing assistance apparatus to draw gas exhaled by a patient toward the sensor, such that exhaled gas can come into contact with the detecting material.

Preferably, in use the attachment end, when attached to a part of a resuscitator system, aligns the elongate body with apertures with flow of gas from the inlet to the breathing assistance apparatus.

Preferably the breathing assistance apparatus is, or forms a part of, a resuscitator system.

Accordingly, in a further aspect the invention can be said to broadly consist of a breath indicator as part of a resuscitator system for an infant that supplies gases to an infant via a face mask, comprising: an elongate body having a sensing end and an attachment end, said sensing end comprising detecting material which changes between two visual indicator states, a first visual indicator state relating to an inhalation phase of the infant, and a second visual indicator state relating to an exhalation phase, the detecting material capable of changing between the visual indicator states at a sufficient rate to substantially correspond to inhalation and exhalation changes of the infant to indicate inhalation and exhalation, said elongate body adapted so that in use, said sensing end can be located proximate to the mouth and/or nose of said infant.

Preferably the sensing end comprises CO2 detecting material which can change colour from a base colour being the first visual indicator state to a detection colour being the second visual indicator state when exposed to gases which have CO2 concentration greater than that normally found in atmospheric air, and back to the base colour when exposed to gases which have CO2 concentrations the same or similar to those found in atmospheric air, so as to allow a medical professional viewing said first end to detect end-tidal or breath-by-breath CO2 present within said breathing assistance apparatus in use.

Preferably said breath indicator further comprises a stopping flange located partway along said elongate body and extending substantially perpendicularly from said body, said flange located between said attachment end and said sensing end.

Preferably the detecting material changes colour from a base colour to a detecting colour when exposed to gases having a concentration by volume of at least 5% or more CO2.

Preferably said attachment end is formed as a handle portion that includes a handle flange extending outwards perpendicularly from the end of said attachment end.

Preferably said sensing end is formed as a hollow section, said hollow section filled with an indicator dye, the wall or shell of said hollow section having pores to allow gases to pass through said wall or shell and contact said indicator dye, said wall or shell substantially clear or translucent to allow a user to view the colour of the dye through said wall or shell.

Alternatively said detecting material is a layer of indicator dye applied to the outside surface of said sensing end, said detecting material applied to at least part of the area of the elongate body near said sensing end.

Alternatively wherein said sensing end is at least partly and preferably wholly formed from detecting material and attached or connected to the remainder of said elongate body.

As a further alternative said detecting material is applied to the entire area of said elongate body.

Preferably said detecting material is a layer of material infused with a CO2 detecting material and applied to the outside surface of said sensing end.

Preferably said indicator has an outer diameter between 1 mm and 5 mm, said indicator also having a length of about 30 mm to about 60 mm, and said elongate body being substantially smooth to not increase the resistance to flow.

Preferably said elongate indicator includes a plurality of apertures in said indicator Preferably said apertures are preferably arranged in a honeycomb pattern.

Preferably said apertures may be any shape including circular, oval, square, rectangular or triangular.

Preferably said apertures are positioned adjacent said attachment end of said indicator.

More preferably said apertures are positioned about 1 mm to about 15 mm away and preferably about 7 mm to about 10 mm away from said attachment end along said elongate body.

Alternatively said apertures are positioned adjacent to said sensing end.

In the alternative said apertures are positioned anywhere from about 1 mm to about 15 mm away but preferably about 7 mm to about 10 mm away from said sensing end along said elongate body.

Preferably in use said indicator is inserted into a breathing assistance apparatus that supplies gases to an infant, such that said sensing end is located proximate to the mouth and nose of the infant and such that said apertures are positioned in a flow of gases from an inlet of the breathing assistance apparatus, wherein use gases from the inlet flow through said apertures creating suction in said breathing assistance apparatus to draw gases exhaled by an infant toward said indicator such that exhaled gases can come into contact with said detecting material.

Preferably said apertures are further positioned to reduce the resistance of the flow of gases from the inlet.

Preferably in-use the locking feature positions the apertures such that the apertures are aligned with the flow of gases from the inlet and/or such that said apertures are positioned to reduce the resistance of the flow of gases from the inlet.

In another aspect the invention can be said to broadly consist of a breathing assistance apparatus for use as part of a resuscitation system for an infant, the breathing assistance apparatus comprising: a manifold section, said manifold section hollow to define a gases space, a gases inlet passing from outside said manifold section into said gases space, said gases inlet adapted for connection to a gases conduit or similar to receive a continuous flow of gases at a pressure above atmospheric and further adapted to allow said continuous flow of gases to enter said gases space, said continuous flow of gases forming a gases stream, a gases outlet from said manifold, in use said gases stream passing through said outlet to a user or patient, a device inlet on said manifold section adapted to allow items to pass into said gases space from outside said manifold section, a breath indicator formed from an elongate body having a sensing end and an attachment end, said sensing end comprising detecting material which changes between two visual indicator states, a first visual indicator state relating to an inhalation phase of the infant, a second visual indicator state relating to an exhalation phase, the detecting material capable of changing between the visual indicator states at a sufficient rate to substantially correspond to inhalation and exhalation changes of the infant to indicate inhalation and exhalation, said breath indicator formed separately from said manifold, said breath indicator disposed into said device inlet so that said sensing end protrudes into said gases space and said sensing end is substantially proximate to at least the gases outlet.

Preferably in-use infant exhales into the outlet and the gases space of the manifold and said breath indicator and said manifold section are mutually sized so that said sensing end in use can be located at or close to an opening of the outlet, such that the sensing end is in the gases path of exhaled gases from the infant.

Preferably at least part of said manifold section is translucent.

More preferably at least that part of said manifold closest to said patient in use is translucent.

Preferably said breath indicator further comprises a stopping flange located partway along said elongate body and extending substantially perpendicularly from said body, said stopping flange located between said attachment end and said sensing end, in use said stopping flange contacting and abutting the perimeter of said device inlet and preventing further travel of said breath indicator through said device inlet.

Preferably wherein the breath indicator is characterised by the sensing end comprises CO2 detecting material which can change colour from a base colour being the first visual indicator state to a detection colour being the second visual indicator state when exposed to gases which have CO2 concentration greater than that normally found in atmospheric air, and back to the base colour when exposed to gases which have CO2 concentrations the same or similar to those found in atmospheric air, so as to allow a medical professional viewing said first end to detect end-tidal or breath-by-breath CO2 present within said breathing assistance apparatus in use More preferably the detecting material changes colour from a base colour to a detecting colour when exposed to gases having a concentration by volume of at least 5% or more CO2.

Preferably said attachment end is formed as a handle portion that includes a handle flange extending outwards perpendicularly from the end of said attachment end.

Preferably a portion of the body of said breath indicator adjacent to said stopping flange and on the side opposite to said sensing end is formed as a handle portion.

Preferably said sensing end is formed as a hollow section, said hollow section filled with an indicator dye, the wall or shell of said hollow section having pores to allow gases to pass through said wall or shell and contact said indicator dye, said wall or shell substantially clear or translucent to allow a user to view the colour of the dye through said wall or shell.

Alternatively said CO2 detecting material is a layer of indicator dye applied to the outside surface of said sensing end.

Alternatively said detecting material is a layer of indicator dye applied to the outside surface of said sensing end of the breath indicator, said detecting material applied to at least part of the area of the elongate body near said sensing end of the breath indicator.

Alternatively said sensing end of the breath indicator is at least partly and preferably wholly formed from detecting material and attached or connected to the remainder of said elongate body.

Alternatively said detecting material is applied to the entire area of said elongate body of the breath indicator.

Alternatively said sensing end of said breath indicator is at least partly and preferably wholly formed from CO2 detecting material and attached or connected to the remainder of said elongate body.

Alternatively said CO2 detecting material is a layer of material infused with a CO2 detecting material and applied to the outside surface of said sensing end of the breath indicator.

Preferably a duck billed valve is located in said device inlet, allowing the passage of items from the exterior to the interior of the manifold section and sealing to prevent the flow of gases from the interior to the exterior of said manifold section during use when no items are inserted, during the insertion of items, for the duration of the time for which the items are inserted, and as the items are removed from the manifold section.

Preferably said breath indicator further has a locking feature, said device inlet further having a fastening feature, said locking feature corresponding with and engaging with said fastening feature in use to retain said breath indicator within said device inlet.

In one form said CO2 detecting is applied to at least part of an inside surface of said manifold section.

Preferably said indicator has an outer diameter between 1 mm and 5 mm, said indicator also having a length of about 30 mm to about 60 mm.

Preferably said elongate indicator includes a plurality of apertures in said indicator Preferably said apertures are preferably arranged in a honeycomb pattern.

Preferably said apertures may be any shape including circular, oval, square, rectangular or triangular.

Preferably said apertures are positioned close to said attachment end of said indicator.

Preferably said indicator is shaped to not increase resistance to the flow of gases through said manifold section.

Preferably in use said apertures are substantially aligned with the flow of gases into the manifold from the inlet such that said apertures are positioned in the flow of gases to create a suction in said breathing assistance apparatus that draws gases exhaled by an infant toward said indicator such that exhaled gases can come into contact with said detecting material.

More preferably said apertures are further positioned to reduce the resistance of the flow of gases from the inlet.

Preferably said manifold section comprising a PEEP outlet opening from manifold to said atmosphere, said PEEP outlet including an aperture opening to atmosphere, said PEEP outlet capable of being occluded and unoccluded manually or automatically, said PEEP outlet positioned substantially opposite to said inlet, gases flowing from said inlet to and out of said PEEP outlet when said PEEP outlet is unoccluded, said gases flowing through said apertures in said indicator and around said indicator, said flow of gases through said apertures causing a drop in pressure across said indicator or due to changing velocities of said gases flow, suction caused from said outlet toward said device inlet, said suction causing any exhaled gases from said infant to be drawn toward said indicator.

Preferably in use said locking feature positions the apertures in the flow of gases such that the apertures are positioned to reduce the effect on flow resistance of the flow of gases from the inlet.

In yet another aspect the invention can be said to broadly consist in a breath indicator as part of a resuscitator system for an infant that supplies gases to an infant via a face mask, comprising: a body having a sensing portion and an attachment portion, said sensing portion comprising detecting material which changes between two visual indicator states, a first visual indicator state relating to an inhalation phase of the infant, and a second visual indicator state relating to an exhalation phase, the detecting material capable of changing between the visual indicator states at a sufficient rate to substantially correspond to inhalation and exhalation changes of the infant to indicate inhalation and exhalation, where in use said indicator is inserted into a breathing assistance apparatus that supplies gases to an infant, such that said sensing portion is located proximate to the mouth and nose of the infant and such that said apertures are positioned in a flow of gases from an inlet of the breathing assistance apparatus, wherein use gases from the inlet flow through said apertures creating suction in said breathing assistance apparatus to draw gases exhaled by an infant toward said indicator such that exhaled gases can come into contact with said detecting material.

In yet a further aspect the invention is said to broadly consist in a breathing assistance apparatus for use as part of a resuscitation system for an infant, the breathing assistance apparatus comprising: a manifold section, said manifold section hollow to define a gases space, a gases inlet passing from outside said manifold section into said gases space, said gases inlet adapted for connection to a gases conduit or similar to receive a continuous flow of gases at a pressure above atmospheric and further adapted to allow said continuous flow of gases to enter said gases space, said continuous flow of gases forming a gases stream, a gases outlet from said manifold, in use said gases stream passing through said outlet to a user or patient, a device inlet on said manifold section adapted to allow items to pass into said gases space from outside said manifold section, a breath indicator formed from a body having a sensing portion and an attachment portion, said sensing portion comprising detecting material which changes between two visual indicator states, a first visual indicator state relating to an inhalation phase of the infant, and a second visual indicator state relating to an exhalation phase, the detecting material capable of changing between the visual indicator states at a sufficient rate to substantially correspond to inhalation and exhalation changes of the infant to indicate inhalation and exhalation, where in use said indicator is inserted into a breathing assistance apparatus that supplies gases to an infant, such that said sensing portion is located proximate to the mouth and nose of the infant and such that said apertures are positioned in a flow of gases from an inlet of the breathing assistance apparatus, wherein use gases from the inlet flow through said apertures creating suction in said breathing assistance apparatus to draw gases exhaled by an infant toward said indicator such that exhaled gases can come into contact with said detecting material.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

The term "comprising" as used in the specification and claims, means "consisting at least in part of". When interpreting a statement in this specification and claims that includes "comprising", features other than that or those prefaced by the term may also be present. Related terms such as "comprise" and "comprises" are to be interpreted in the same manner.

The invention consists in the foregoing and also envisages constructions of which the following gives examples.

BRIEF DESCRIPTION OF THE DRAWINGS

One preferred form of the present invention will now be described with reference to the accompanying drawings in which:

FIGS. 11, 12 and 13 show in more detail the breath indicator attached to the T-piece of FIG. 10.

DETAILED DESCRIPTION OF THE PREFERRED EMBODIMENT

Figure 1:
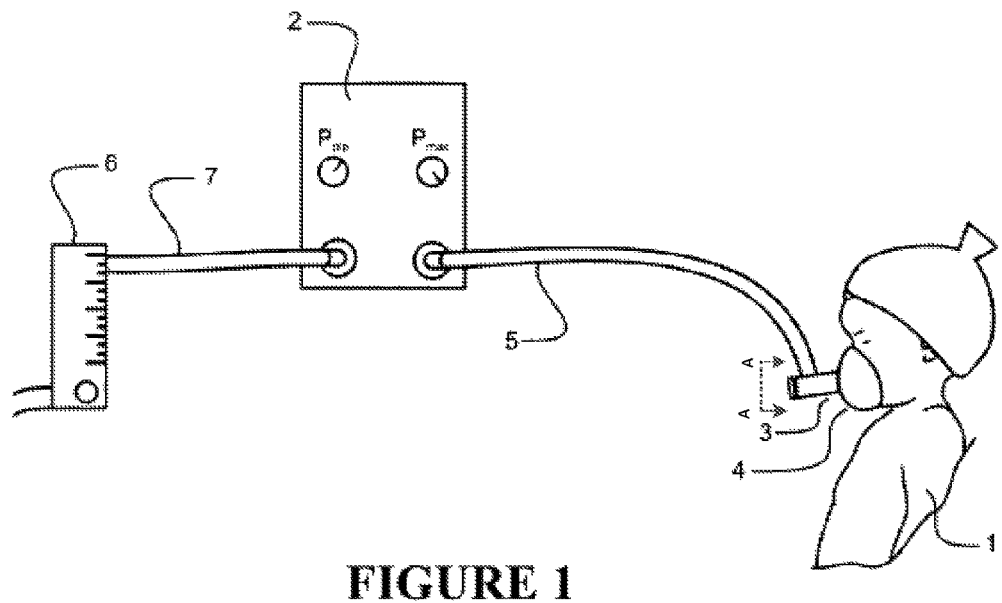
FIG. 1 shows a representation of a typical system for resuscitating infants as is known in the art, with an infant (or neonate) receiving gases from a resuscitator that forms part of the system, the gases passing from the resuscitator to the infant via a manifold section, the manifold section connected to the resuscitator via a conduit that allows the gases to pass from the resuscitator to the manifold section.

FIG. 1 shows a representation of a typical resuscitator system as is known in the art, with a neonatal infant 1 receiving gases from a resuscitator 2 that forms part of the system. The gases are passed on to the infant 1 via a manifold section 3 which is in use connected to a patient (such as an infant) interface or mask section 4. The manifold section and resuscitation system may be used with a mask or an endotracheal (ET) tube. The embodiments described below will be described with respect to a mask attached to the manifold, but it should be appreciated the use of such a breath indicator may be used in conjunction with ET tubes or other patient interfaces, such as face masks, nasal masks, oronasal masks, various configurations of nasal prong(s), and their associated connections or components.

It should be appreciated reference to a patient interface may comprise any one or combination of the following types: a face mask, an oral mask, an oronasal mask, a nasal mask, one or a pair of nasal prongs, an endotracheal tube, a T-piece resuscitator apparatus, gas flow regulator or gas pressure regulator associated with any one or more of these, although this list should not be seen as limiting.

The use of a mask with the resuscitation system is not to be considered limiting; it is simply an example as described by the following. The manifold section 3 is connected to the resuscitator 2 via a conduit 5 that allows the gases to pass from the resuscitator 2 to the manifold section 3. In the embodiment shown, the resuscitator 2 is connected to a pressure regulator 6 via a gases supply conduit 7, the resuscitator 2 receiving gases from the pressure regulator 6 via the supply conduit 7, the pressure regulator fluidly (or gaseously) connected to a remote gases supply via a wall socket or similar. The pressure regulator 6 provides gases to the resuscitator 6 at 50 psi or thereabouts. In alternative embodiments, the resuscitator could be a self-contained unit which draws in gases directly from atmosphere and passes these on to the infant 1 via the conduit 5. The gases or air supply are provided at a pressure above or at atmospheric pressure. The delivered pressure is varied between Peak Inspiratory Pressure (PIP) and Peak End Expiratory Pressure (PEEP) by the occlusion of a PEEP outlet (described later). The PIP is adjusted at the resuscitator 2 to a desired level. The system shown above may also be used for respiration and assisted respiration (ventilation) of a neonate or infant.

Breathing Assistance Apparatus

Figure 2:
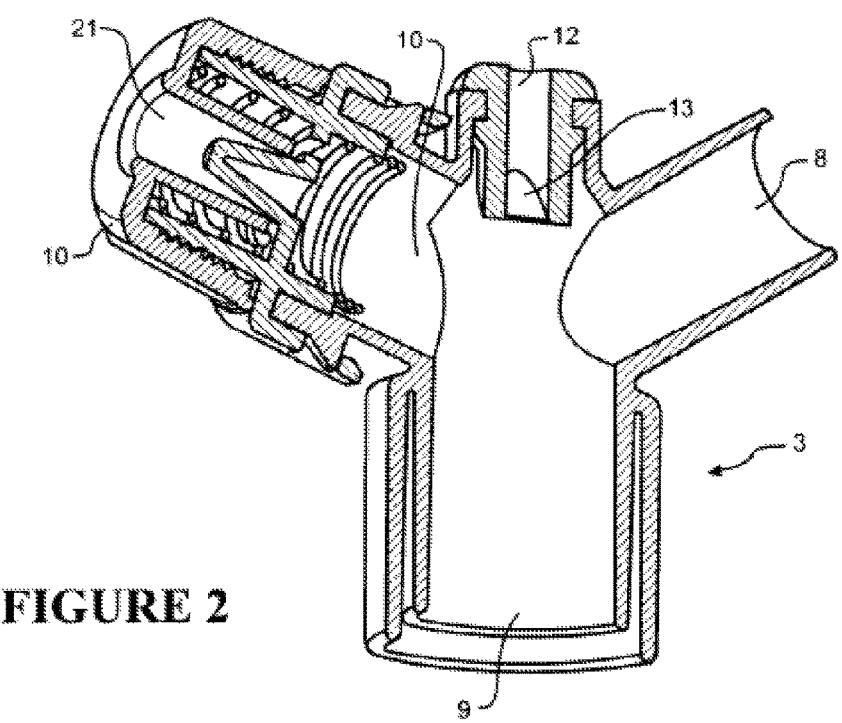
FIG. 2 shows a cut-away view cut along line A-A of the manifold section of FIG. 1 in more detail, the manifold section having a gases inlet which in use receives gases from the resuscitator, a gases outlet which in use passes the gases to an infant via a connected mask section (not shown), a device inlet which allows the passage of items such as suction tubes from the exterior to the interior of the manifold, and a PEEP outlet with a cap.
Figure 3:
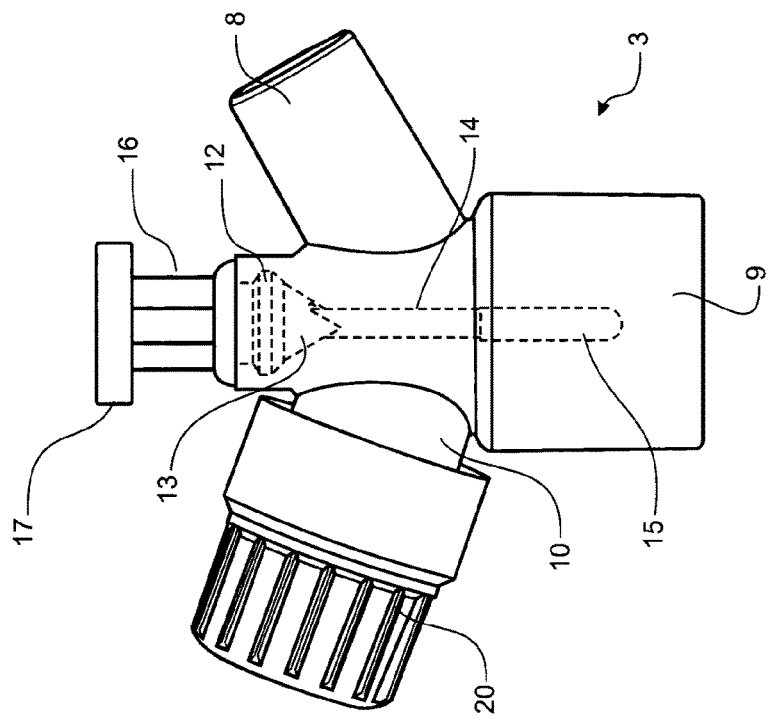
FIG. 3 shows a view of the manifold section of FIGS. 1 and 2 with a CO2 breath indicator that forms part of the present invention located in the device inlet, the breath indicator being shown as hidden detail because it is inserted into the manifold.
Figure 5:
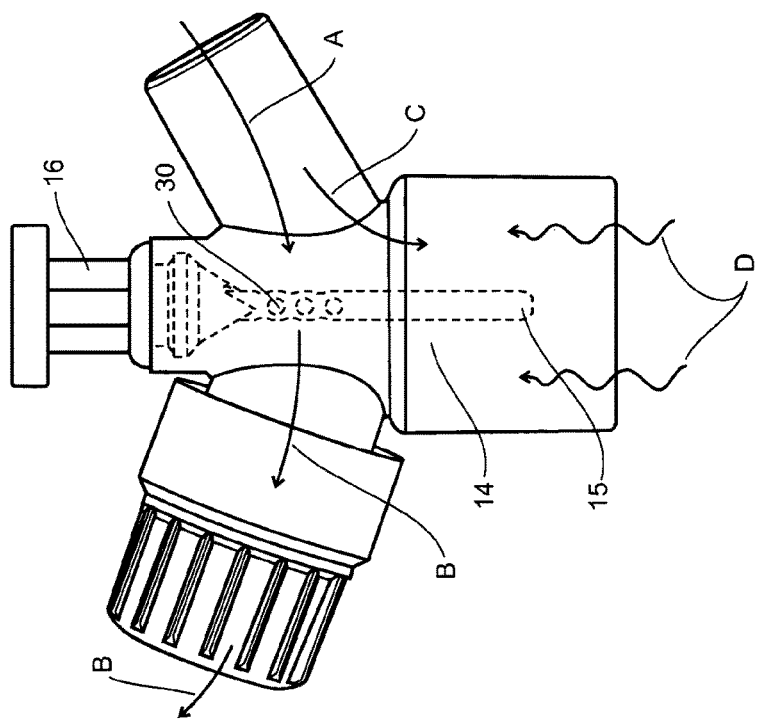
FIG. 5 shows a view of the manifold and breath indicator as shown in FIG. 4 with flow lines showing gases flow when the PEEP outlet is unoccluded, gases flow then the PEEP outlet is occluded and the movement of exhaled gases from an infant.
Figure 10:
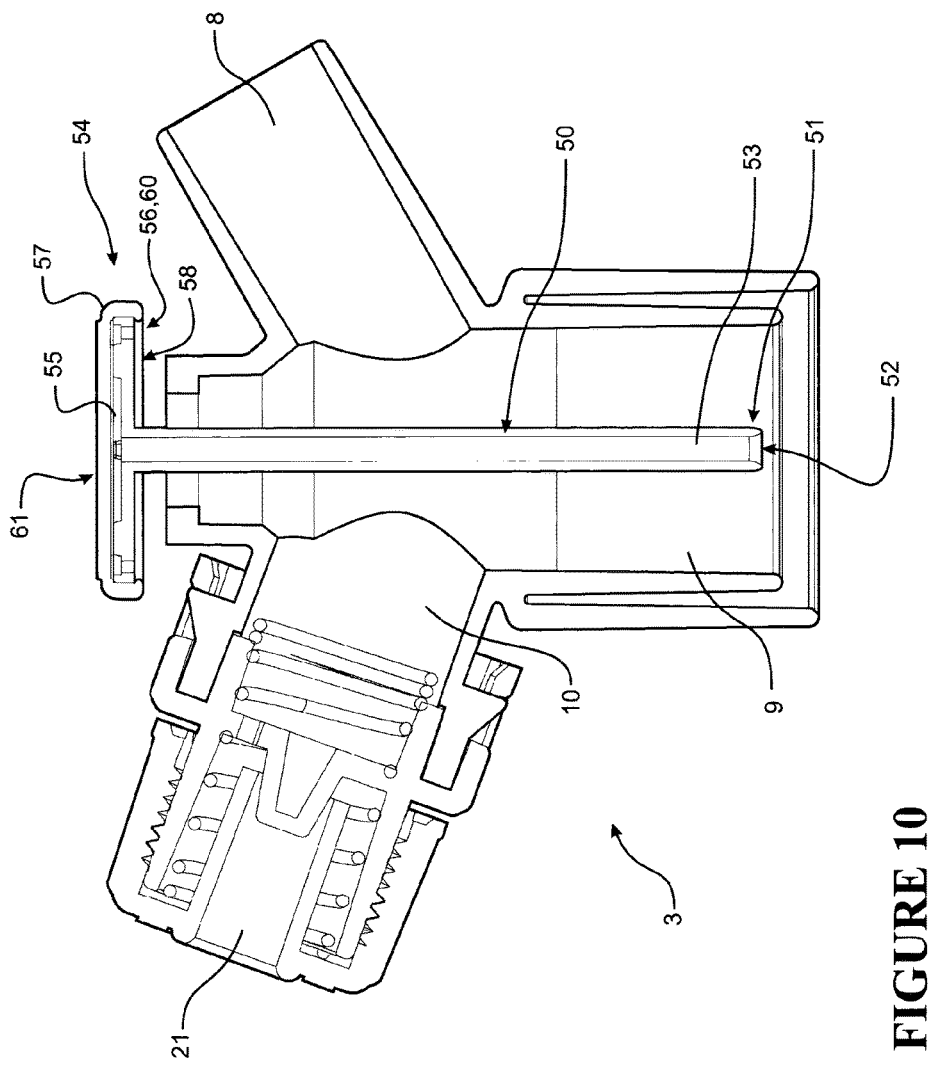
FIG. 10 shows a further embodiment of a breath indicator received by and attached to a T-piece, such a breath indicator as shown by FIGS. 11-13.

FIGS. 2 and 3 and show a preferred form of the manifold 3 (and is further shown in FIGS. 5, 10). The main body of the manifold section 3 is preferably substantially cylindrical in shape, with a plurality of inlet and outlet ports or port passages. The manifold section 3 is hollow and defines a gases space. The gases space forms gases connections between the inlet and outlet ports.

With reference to FIG. 2, the preferred form of manifold section 3 has a gases inlet 8 which in use is connected to the conduit 5 so that gases from the resuscitator 2 pass along the conduit 5 and are provided to the hollow interior of the manifold section 3. In use, the gases pass from the inlet port 8, through the hollow interior of the manifold section 3 and then exit the manifold section 3 via the gases outlet 9. In the embodiment shown, the gases outlet 9 is connected to a detachable mask section 4 or similar (shown in FIGS. 1, 8, 9), the mask section 4 in use fitting around the nose or the nose and mouth of the patient (e.g. infant) 1, so that gases exiting the manifold section 3 via the gases outlet 9 pass to the patient 1 via the mask section. An example of a suitable mask section is disclosed in U.S. D574,487. All of the passages are defined by solid walls.

Also shown in FIG. 2 (with similar configuration also shown in FIG. 10) is a pressure relief section or over pressure relief section that forms part of the manifold section 3. The preferred embodiment of pressure relief section comprises a PEEP outlet passage 10 (PEEP outlet 10) passing outwards from the main body of the manifold section 3, with an aperture that opens to atmosphere located at or towards the outer end of the PEEP outlet 10. A cap 20 is positioned on the end of the passage 10 and may be used to adjust the valve mechanism. The cap 20 includes an aperture in it that allows gases to exit through the cap. The cap is moveable and can be moved to adjust the size of the aperture in order to control PEEP value.

The cap 20 includes an aperture 21 within the cap. The aperture in the cap can be occluded and unoccluded to control PEEP. In use a substantial portion, if not all of the gases from the inlet port 8, flow out of the second outlet passage 10 when the aperture is open and uncovered. Only a small or no portion of the inlet gases reaches the PEEP outlet if the aperture in the cap is uncovered. In use, the aperture in the cap can be covered and closed or occluded to force the gases flowing into the inlet port to flow out of the PEEP outlet 9 and to the patient (e.g. infant).

The aperture is can be opened and closed manually by a medical professional or user of the device using a finger or any other suitable body part or other suitable instrument. The delivered gases are varied between the PIP when the aperture 21 is occluded and the PEEP when the aperture 21 is unoccluded. The cap aperture 21 is opened and closed regularly to vary the PIP and PEEP at the normal rate of breathing to resuscitate a patient (e.g. infant). The opening and closing of the cap aperture provides gases to the patient (e.g. infant) in a cyclic manner. The opening and closing or occluding of the cap aperture allows a user (such as medical professional) to simulate breathing of the patient (e.g. infant) for resuscitation or assisted breathing purposes. The manual occlusion of the cap aperture also allows the user to control the amount and frequency of gases delivery to the patient.

In addition a valve mechanism (not shown) may be positioned in association with the passage 10 and the aperture. The valve mechanism is adapted to control the flow of gases passing from the interior of the manifold section 3 to atmosphere so that the pressure in the manifold will not rise above a certain preset level. If the pressure rises above such a level, the valve advantageously activates in such a manner that excess gases are vented from the manifold 3 and the pressure is limited.

Several types of valves are suitable for use as part of the pressure relief section, for example umbrella valves, jet valves, and so on. The purpose of the pressure relief section is to allow excess gases to be vented in the event of potentially harmful pressure build-up within the interior of the manifold section 3. In a preferred form there is no valve present in the second outlet passage 10. In an alternate form the valve mechanism may be adapted to maintain the PEEP level reasonably constant. The valve may be similar to that described in U.S. Pat. No. 7,341,059.

A device inlet 12 is also shown as part of the manifold section 3. In one embodiment, the device inlet is located directly opposite the PEEP outlet 9. The device inlet 12 is intended to allow items such as suction tubes or similar to be inserted into the interior of the manifold section 3 during use, so that these items can then, if necessary, pass through the interior of the manifold section 3 to be inserted into the airways of the infant 1. The device inlet 12 can include a valve or similar which allows the passage of items from the exterior to the interior of the manifold section 3, but which seals to prevent the flow of gases from the interior to the exterior both during use when no items are inserted, and during the insertion of items. In one form the device inlet 12 includes a duck billed valve 13.

The duck billed valve 13 is normally sealed, but upon insertion of e.g. a catheter, the duck-billed valve 13 opens to allow the catheter end to be received and enter the interior of the manifold section 3. The bill of the duck billed valve 13 seals around the end of the inserted item (e.g. a catheter), thereby helping ensure that the manifold section 3 remains sealed against inadvertent gases leaks. Accordingly, in one embodiment, the duck billed valve can be used to receive a breath indictor 14, 54.

Breath Indicator

The preferred form of breathing assistance apparatus also has a separate breath indicator 14, 54 which is a separate item to, and used in conjunction with, the manifold section 3. Such indictors 14, 54 are removable from the breathing assistance apparatus.

In the general sense the breath indicator 14 comprises a body, having a sensing portion and an attachment portion. The sensing portion comprises a material or structures that switched between two visual indicator states.

The first visual indicator state relates to inhalation and the second visual indicator state relates to exhalation by the patient.

The detecting material or structures are capable of changing between the visual indicator states at a sufficient rate to substantially correspond to inhalation and exhalation changes of the infant to indicate inhalation and exhalation.

The indicator body may have included other structure that reduced the indicator's resistance to flow.

The attachment end portion 16, 56 of the indicator may have included features or structures to allow the indicator to be held in the breathing assistance apparatus, in use. The attachment end portion 16, 56 may also have included structures to align the indicator's elongate body in the correct orientation and position within the breathing assistance apparatus, or patient interface as necessary.

The breath indicator 14 will now be described with particular reference to FIGS. 3 to 6.

Figure 4:
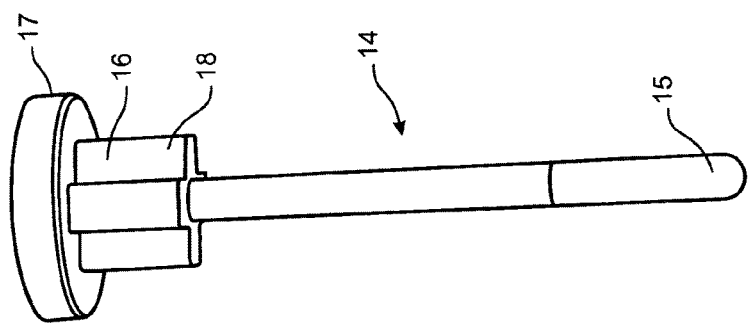
FIG. 4 shows the breath indicator of FIG. 4 by itself.

As it is shown in FIG. 3, the manifold section is oriented so that the gases outlet 9 is at the lowest point, and the device inlet 12 is at the top of the device, directly above the gases outlet. This orientation generally corresponds with how the device will be oriented in use, with an infant 1 lying on their back facing upwards and the gases outlet 9 directly above their nose and mouth. The description below will assume this 'in-use' orientation for the purpose of describing the relationship of various features to one another. However, no other significance should be read into the use of terms such as, for example, 'above', 'below', 'top' and 'bottom' when used in this specification. These are merely intended to convey a relative relationship for a specific orientation—such as that which is shown in FIG. 4.

In one embodiment, the elongate body of the breath indicator 14 generally has the form of an elongate cylinder. The elongate body has a sensing end 15 and an attachment end 16. One end of the elongate body is formed as or is connected to a sensing end 15 and the other end is formed as or is connected to an attachment end 16. The sensing end 15 will be described in detail below.

In various forms, the elongate body may be formed from a rigid plastic such as a polycarbonate.

In use, and for example as shown in FIG. 3, the sensing end 15 is inserted through the device inlet 12, with the duck billed valve 13 sealing around the elongate body of the breath indicator 14 to maintain gases pressure integrity within the manifold section 3. The same configuration would apply in relation to breath indicator 54 when being inserted through the device inlet 12 and duck billed valve 13.

The indicator 14 may be about 30 mm to about 60 mm in length, or may be a length of about 50 mm. The actual length will depend on the size of the breathing apparatus or patient interface to which the indicator 14 (or 54) is to be attached.

The indicator 14 may have an outer diameter of about 1 mm to about 5 mm, or may be about 3 mm. The actual diameter will depend on the size of the inlet of the breathing apparatus or patient interface through which the indicator 14 (or 54) is to be inserted.

The elongate body of the indicator 14 (or 54) may be of a reasonably smooth surface along its length. The small outer diameter relative of the elongate body to the size of the gases space means the breath indicator 14 (or 54) does not need to occupy much room in the gases space. The shape of the elongate body may also go some way toward not increasing the resistance to the flow of gases in the gases space. The smooth shape of the body may contribute to not increasing the resistance to flow of gases in the gases space.

It should be noted that sensing end and attachment end as referred to in this specification in relation to the indicator 14 are defined as the respective ends of the indicator's 14 elongate body. It should also be noted that sensing end and attachment end 16 also encompass a distance of about 1 mm to about 15 mm from either of the respective ends. The meaning adopted is dependent on context. In the general sense when sensing end or attachment end is used in the specification, it is meant the ends of the elongate body or at least the general area of the elongate body around the ends, specifically in relation to the indicator 14.

Sensing End

In use, the sensing end 15 of the indicator 14 comprises a detecting material that changes between two visual indicator states.

The indicator 14, 54 provides for a visual indicator and the detecting material can change between two visual states. A visual indicator state is a physical visual state of the detecting material of the sensing end 15 or sensor 55 (not shown) for the indicator 14 or 54, respectively.

A visual indicator state is noticeable or observable (i.e. optically detectable) to a human eye and the difference between two visual indicator states is also noticeable to the eye (or may be other optically sensing equipment).

The indicator 14, 54 is adapted to detect inhalation and exhalation of an infant and visually signal inhalation, exhalation and the change between the inhalation and exhalation states. The detecting material changes between a first state, relating to inhalation phase and a second state, related to an exhalation phase. The detecting material is adapted to change states at a rate to substantially match inhalation and exhalation. The detecting material is preferably colorimetric, meaning the detecting material changes colour as it changes between the two states of inhalation and exhalation. The preferred way of detecting inhalation and exhalation is to sense the amount of $CO_2$ present.

In one embodiment form, the sensing end 15 of indicator 14, or sensor 55 of indicator 54, is formed and adapted so that it will rapidly change colour in the presence of $CO_2$ concentrations above those normally found in atmospheric gases—i.e. it will change colour when it comes into contact with exhaled air from a person. The sensing end 15 of indicator 14, or sensor 55 of indicator 54, is also formed and adapted so that it will change colour rapidly, if not almost instantaneously. Once the $CO_2$ concentration reduces back to, or close to, that of atmospheric air, the sensing end will return to its original colour from the detection colour. In this manner the sensing end 15 of indicator 14, or sensor 55 of indicator 54, is capable of changing from a resting or base colour when exposed to atmospheric air, to a second colour or detection colour when exposed to $CO_2$, and back again to the resting colour once the $CO_2$ concentration diminishes, and it is most preferred that the colour change takes place rapidly enough to roughly match the inhalation/exhalation cycle of the infant 1. That is, rapidly enough to detect end-tidal or breath-by-breath Carbon Dioxide ($CO_2$) in the breath of an infant. It is preferred that the colour change takes place when the indicator dye or indicator material is exposed to $CO_2$ concentrations of 5% or above by gases volume.

There are several ways in which the sensing end 15 of indicator 14, or sensor 55 of indicator 54, could be formed.

In one form of indicator 14, the sensing end 15 is formed as a hollow section which holds an indicator dye. The wall or shell of the hollow section has pores to allow gases, and especially exhaled gases with a high concentration of $CO_2$ to come into contact with the indicator dye. In use, the indicator dye changes colour when the $CO_2$ concentration rises above that normally found in atmospheric air, and a user can view this colour change through the wall of the manifold section 3 and the wall of the hollow section which holds the indicator dye.

In an alternative embodiment, the sensing end 15 is formed by applying a layer of indicator dye, or a layer of material infused with an indicator dye, to the outside surface of at least the sensing end of the elongate cylindrical shaped body.

Alternatively the indicator dye or indicator material may be applied to the rod or elongate body of indicator 14 in any other suitable way that allows $CO_2$ from the infant's exhaled air to come into contact with the indicator.

As outlined above, the indicator dye or indicator material changes colour when the $CO_2$ concentration rises above that normally found in atmospheric air, and a user can view this colour change through the wall of the manifold section 3 and if the dye is held in a hollow section, the wall of the hollow section which holds the indicator dye.

In a yet still further alternative, at least the lower end part of the elongate cylinder may itself be formed from a $CO_2$ detecting material, attached or connected in any suitable manner to the remainder of the breath indicator 14.

Figure 6:
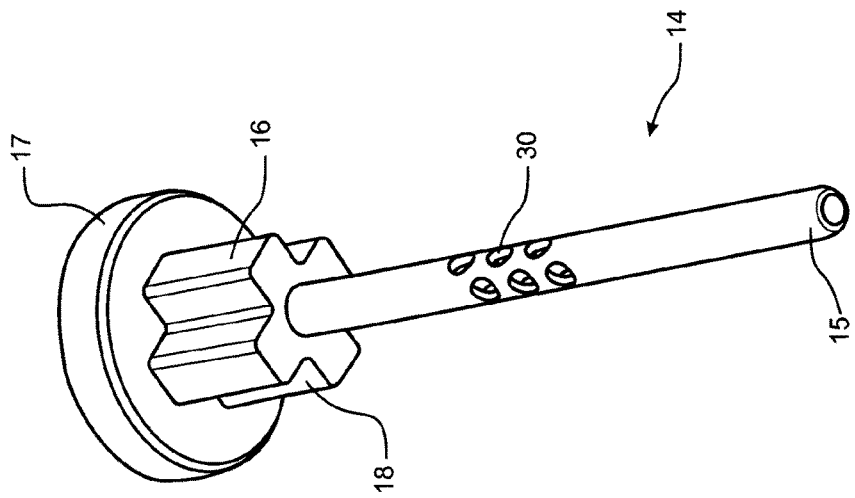
FIG. 6 shows a view of the breath indicator with apertures in the breath indicator to allow gases flow through the breath indicator when the PEEP outlet is unoccluded.

A further alternative form of the indicator 14 is shown in FIG. 6. As shown in FIG. 6, the apertures 30 are positioned or formed in the upper part of the indicator 14. The apertures 30 are in the part of the indicator that is closest to the duck billed valve 13, meaning the aperture 30 are closer to the attachment end than the sensing end. The apertures may be about 1 mm to about 10 mm away from the duck billed valve. Alternatively, the apertures may be closer to the sensing end 15, for example may be about 1 to about 10 mm away from the end of the indicator 14. As a further alternative, the apertures 30 may be positioned at any other positions along the indicator 14, this form not being shown in the figures.

The apertures 30 of indicator 14 can be hexagonal in shape and arranged, for example, in a honeycomb shape. Alternatively, the apertures 30 may be any other suitable shape such as diamond shaped, rectangular, oval, circular etc. FIG. 6 shows the apertures 30 may be arranged in a honeycomb structure. The indicator 14 may be hollow with detector material inside the tube. Or, the detector material may be separately, or in addition, applied to the outside of the indicator 14 body near the sensing end 15.

When the cap aperture 21 is unoccluded the gases received in the inlet port 8 pass through the apertures 30 and out of the cap aperture 21. This is shown by arrows A and B in FIG. 5. The gases from the gas supply (arrow A) are received by the inlet port 8 and pass through the apertures 30 and out through the cap (arrows B). When the cap aperture is occluded the gases received by the inlet port 8 (arrow A) pass out through the gases outlet 9 and to the infant (as shown by arrow C). The gases exhausted out of the PEEP outlet 10 and cap aperture cause the gases exhaled by the infant to be drawn upward and into the indicator through the apertures 30 (shown by arrows D). The gases exhaled by the infant enter the manifold 3 through the gases outlet 9 (arrows D), since the infant exhales into the mask 4 or ET tube (not shown) and the gases outlet 9. The exhaled gases are drawn upward due to a combination of venturi and Bernoulli or simply venturi or simply Bernoulli Effect. These effects are caused by the pressurised gases (therapy gases) flowing from the inlet port 8 to the secondary outlet port 10 through the apertures 30. The pressurised gases flowing through the apertures causes a pressure drop across the holes and from one side of the indicator to the other. It is this pressure drop that causes exhaled gases from the infant to be drawn toward the $CO_2$ detecting material. The gases exhaled by the infant are continuously drawn or sucked into the indicator where they come into contact with the $CO_2$ detecting material and cause the $CO_2$ detecting material to change colour in the presence of $CO_2$ present in the exhaled gases of the infant. The suction created by the pressurised gases passing through the apertures 30 of indicator 14 may help to increase the sensitivity and response rate of the breath indicator 14. The system may be optimised based on the whole pattern design and by varying the size of the apertures. The apertures 30 can, as mentioned earlier, be hexagonal and arranged in a honeycomb pattern. Alternatively, the apertures 30 maybe any other suitable shape like square, rectangular, oval or circular.

The apertures 30 are advantageously positioned along the body of the indicator 14. At least some of the apertures are preferably positioned such that they are aligned with the flow of gases from the inlet. The apertures 30 may help reduce the resistance to flow of gases created by the elongate indicator being in the gases space 3. The apertures 30 being aligned with the flow of gases reduces the resistance to flow the flow of gases due to the apertures 30 and further reduces the resistance to flow of gases due to the presence of the indicator 14.

Detector Material Composition

As outlined above, in one embodiment, the indicator 14, 54 comprises a $CO_2$ detector material in the form of a coloured dye or coloured material that changes colour in the presence of $CO_2$. The dye or material is capable of changing colour in the presence of $CO_2$ from the exhaled air of an infant or infant. The change in colour corresponds to a particular visual indicator state. Most preferably the dye changes colour when the infant's exhaled breath has at least 5% $CO_2$ by gases volume. The indicator dye does not change colour in concentrations less than 0.5% $CO_2$ hence the dye does not change colour due to $CO_2$ in the atmosphere. The most preferred composition of dye is blue when it is not exposed to $CO_2$ or when the concentration of $CO_2$ is less than 0.5%. The dye changes from a blue to a yellow colour when it is exposed to $CO_2$ concentrations of 5% or above. Alternatively any other colour change is acceptable. A blue to yellow colour change is preferred since it is very visible to a medical professional that may be monitoring the breathing of the infant. The blue to yellow colour change provides a visual indication to an observer of the infant's breathing. The dye preferably changes colour due to a chemical reaction between the dye and the $CO_2$. The reaction is reversible and the dye changes colour back to blue when the $CO_2$ concentration drops below 5%. The reversible reaction allows for a breath by breath indication, meaning each time the infant exhales the dye changes from blue to yellow and the each time the infant ceases exhaling, and the indicator's sensing end 15 of indicator 14, or sensor 55 of indicator 54, is exposed to atmospheric gases, the dye changes from yellow to blue. Breath by breath indication is advantageous because it allows a medical professional to monitor the infants breathing and ensure the infant is breathing correctly. The blue colour of the detecting material represents the first visual indicator state. The blue colour (first visual indicator state) corresponds to the inhalation of an infant. The yellow colour of the detecting material represents to the second visual indicator state. The yellow colour (second visual indicator state) corresponds to exhalation from the infant.

The detecting material may undergo intermediate visual indicator state changes. The intermediate states occur as the detecting material changes between the first and second visual indicator state. Preferably there are two intermediate visual indicator states. Alternatively there may be any other number of intermediate visual indicator states. The detecting material preferably goes through a green phase and yellow green phase as it changes colour from blue to yellow. The green phase occurs when the $CO_2$ concentration is approximately between 1% and 2%. A yellow green coloured state occurs when the concentration of $CO_2$ is between approximately 2% and 5%. The detecting material (indicator) changes colour to a yellow colour when the concentration of $CO_2$ is above approximately 5%. The concentration of $CO_2$ in the room air is generally around 0.03%. The preferred detecting material remains permanently yellow coloured if it is damaged or malfunctioning. This allows a user or a medical professional or supervisor of therapy to see if the indicator is damaged or malfunctioning. The breath indicator 14, 54 can be changed. Preferably the optimal time of use of the indicator 14, 54 is up to 24 hours, but this will depend on how much use the detecting material can take before it is exhausted. If the indicator is used for longer than 24 hours, the colour of the detecting material eventually fades to a yellow-light green colour—this may be useful as a further visual indicator to the user for indicating when the sensor or detecting material is nearing its end of life or exhaustion point.

The indicator dye can be formed from any suitable dye such as, for example, metacresol purple or bromothymol blue. Any other suitable dye may also be used as an alternative. The dye must be a colour that is easily visible to the human eye when activated. The number of visual indicator states that may occur are dependent on the type of dye or material used as the detecting material. The invention visually represents inhalation and exhalation of an infant, with a clear visual state change between the inhalation phase and exhalation phase of the infant. The purpose of the indicator is to visually show or signal inhalation and exhalation of an infant being resuscitated or ventilated to allow a medical professional to determine if an infant is breathing correctly or if the infant has been resuscitated.

In alternative forms the indicator's sensor end 15 or sensor 55 may be formed from, or may include, any other suitable substance to act as a CO2 detector. In one form the sensing end 15 or sensor 55 of the breath indicator 14 or 15 respectively, may be formed or comprise a powder or grains of pH sensitive material. In other forms, the sensing end 15 or sensor 55 of the indicator 14, 54 respectively, may be in the form of pH sensitive paper, such as litmus paper. Alternatively, the indicator's detecting material substance may be any other pH sensitive material that is known to persons skilled in the art, for example, phenol red, cresol blue, phenolphthalein, thymol blue, bromthymol blue and so on. In a further alternative form, the indicator's detecting material with sensing end 15 or sensor 55 for indicators 14 or 54 respectively, or may include substances that absorb and react with gaseous carbon dioxide to produce a colour change. Examples of such materials include, but are not limited to, are barium oxide, lithium hydroxide, calcium oxide, sodium hydroxide and many others that are known in the art. These CO2 absorbing materials may be in any suitable form for example a lattice, powder, liquid or any other suitable form.

In another alternative embodiment, the indicator 14 or 54 may comprise temperature sensitive materials that change colour in response to a specified temperature change. The purpose of the indicator 14, 54 is to show breathing of an infant by indicating when an infant exhales. Exhaled air is generally at a higher temperature than ambient air. The temperature sensitive material changes colour when there is a predetermined temperature change, hence changing colour when an infant exhales. The temperature sensitive material may be arranged in any suitable form for example a strip, a disc, a powder and so on.

In a further alternative embodiment, the indicator 14 or 54 may comprise a humidity sensor. Medical gases or medical air and oxygen used to resuscitate an infant (or neonate) are generally dry. In most cases, the gases or air or oxygen is humidified to less than 10% moisture content. The exhaled breath from the infant is substantially higher in terms of relative humidity and moisture content. The higher moisture or humidity of the exhaled air causes the indicator to change colour. The humidity sensor preferably only changes colour when there is a predetermined humidity change or when a predetermined level of humidity is reached. The humidity sensor is arranged in any suitable form for example a strip, a disc, a powder, as a rod and so on. The humidity sensor may also be a holographic sensor that may display a plurality of images. One image may correspond to low humidity and hence correspond to the inspiration phase of the infant's breathing. The sensor image may change when there is predetermined change in humidity or when a predetermined level of humidity is reached, signifying exhalation or expiration phase of the infant.

In another alternative form, at least part of the inner surfaces of the manifold may be coated with a CO2 indicating material. Preferably, the CO2 detecting material may be applied or be present on the inner surfaces of the outlet 9. The CO2 indicator may be present on all the inner surfaces of the gases outlet 9 or may only be present on parts of the inner surfaces of the gases outlet 9. Alternatively or in addition, the CO2 material may be present on the inner surfaces of other parts of the manifold for example on the inner surface of the wall that defines the secondary outlet passage 10.

Attachment End

The attachment end 16 of indicator 14, or the attachment end 56 of indicator 54, at the top of the device is formed as a handle to allow a doctor or other medical professional to insert or remove the breath indicator 14, 54 from the manifold section 3. The most preferred form of handle is formed so that a handle flange 17, 57 extends outwards perpendicularly from the top of the attachment end, the handle flange 17, 57 allowing a doctor or user to gain a grip on the attachment end 16, 56 to pull the breath indicator 14, 54 clear of the manifold section 3. If preferred, that part of the body directly below the handle flange 17, 57 can be formed as a knurled or ridged grip for the same reason—to allow a person to grip the handle section more easily.

In the most preferred form, a stopping flange 18, 58 can be located at a mid-point of the elongate body of the breath indicator 14, 54 just below the knurled portion of the attachment end 16, 56. The stopping flange 18, 58 may extend outwards perpendicularly from the body. In use, the sensing end 15 or sampling end 51 is inserted into the device inlet 12 and the elongate body of the breath indicator 14, 54 is pushed through the device inlet 12 until the stopping flange 18, 58 contacts the top surface of the manifold section 3 and is prevented from travelling any further relative to the manifold section 3. The stopping flange is a preferred, but not essential, feature. Mid-point in this context is not intended to a halfway point, merely a point at some location between the two ends.

Locking Feature

In one form, the breath indicator 14, 54 fits into the device inlet 12 by means of a friction fit with the sides of the device inlet 12.

In alternative forms, either the breath indicator 14, 54 or the manifold section 3, or both, can include an optional locking feature that locks the indicator in place when the indicator is inserted into the manifold section 3. The indicator may be attached in place by any suitable connection. For example, a threaded connection, interference click-fit connection, or any other suitable locking mechanism. The locking feature may be a protrusion or a series of protrusions (not illustrated) extending from the elongate body just below the stopping flange 18, 58. The manifold section 3 itself may include at least one corresponding fastening feature to correspond with the locking feature on the breath indicator 14, 54. Such a fastening feature can be positioned on, along, within or around the inlet 12. The mutually adapted fastening features could be, for example, at least one or a plurality of vertically aligned slots (not illustrated) positioned around the device inlet 12, which correspond with at least one or a plurality of ridges on the body of the breath indicator 14, 54.

In another form, the breath indicator 14 can comprise an alignment feature or features (not shown). It should be noted that there may be one or multiple alignment features provided with the breath indicator 14. The alignment feature may form part of the locking feature/features. Alternatively, the alignment feature may be separate to the locking features. The alignment feature acts to provide correct positioning of the breath indicator 14 within the manifold such that at least some of the apertures 30 of indicator 14 are substantially aligned with the gases flow into the manifold 3. The apertures 30 being aligned with the gases flow are advantageous because there is no increased resistance to the flow of gases. The apertures being aligned with the flow may reduce the resistance to flow of gases from the inlet. The apertures 30 allow gases to flow through and hence reduce the resistance to flow due to the indicator being inserted into the gases flow. At least part of the gases flow through the apertures 30 rather than just around the indicator hence reducing the resistance to flow due to the indicator being inserted in a gases flow. The apertures being aligned with the flow of gases further goes in some way to reducing the resistance to flow due to the apertures 20. The apertures 30 being aligned with the flow allow the gases to flow more easily through the apertures and encounter less resistance to flow and fewer obstacles and can adopt a less tortuous path to flow around and/or through the indicator. The apertures 30 being aligned with the flow of gases reduce the resistance to flow of gases from the inlet.

The alignment feature may be any suitable feature. Some examples of an alignment feature are a baffle, a flange, a pin, a screw or any other suitable feature. The alignment feature can be positioned at or near the attachment end 16 of indicator 14. The alignment feature is advantageous because it allows the indicator to be inserted and retained in the correct operational position. The alignment feature also makes using the breath indicator 14 easy for a user, because the alignment feature acts a guide for the correct position of the indicator 14. The breath indicator 14 may also comprise a receiving feature (not shown). The receiving feature may receive the alignment feature to correctly position the indicator, particularly the apertures 30 such that the apertures are substantially aligned with the gases flow into and through the manifold 3.

In Use

As outlined above, the breath indicator 14, 54 is, in-use, inserted through the duck billed valve and the sensing end 15 of indicator 14, and sampling end 51 of indicator 54, extends into the gases space defined by the manifold section 3. In use, the breath indicator 14 and particularly its sensing end 15, or sampling end 51 of indicator 54, is provided at least proximate to (i.e. close, near or substantially adjacent to the region of) the mouth and nose of the infant 1, or region where gas is exhaled by the patient.

The sensing end 15 of indicator 14 can be about 1 mm to about 15 mm away from the nose and mouth of the patient. It should be understood proximate is about 1 mm to about 20 mm, but may be about 1 mm to about 10 mm away.

The sensing end 15 of the indicator 14 is preferably located proximate to at least the outlet 9. It is most preferred that the indicator 14 extends into the manifold section 3 until the sensing end 15 is between 2 mm and 8 mm away from the gases outlet 9. That is, between 2 mm and 8 mm from extending out beyond the gases outlet 9. Most preferably the sensing end 15 is approximately 3 mm away from the gases outlet 9.

In use, the patient (e.g. infant) inhales gases passing out of the gases outlet 9 in a constant stream. The infant 1 will exhale against this constant stream. Most of the exhaled air will be forced around the edges of the mask section 4 to atmosphere. However, a portion will return into the manifold section 3 against the constant flow of gases. As the sensing end 15 of the indicator 14, or sampling end 51 of indicator 54, is positioned as close as possible to the gases outlet 9, there will be a greater concentration of gases at this point than there would be if the sensing end portion 15 or sampling end 51 were located at a point further away from the user's mouth or airways. The sensing end 15 or sampling end 51 is located as close as possible to the user's mouth and nose as possible without actively interfering with therapy.

It can therefore be seen that the sensing end 15, or sampling end 51, being extended into the manifold is advantageous because it allows the sensing end 15 or sampling end 51 to be at the point of most sensitivity and therefore provide an optimised measurement because it is as close as practicable to the patient. The location, or locating, of the sensing end 15 or sampling end 51, as described above, is also advantageous because there is preferentially no increase in dead space within the manifold 3 involved in making the measurement.

If the breath indicator 14, 54 and more specifically the sensing end 15 or sampling end 51 is located in its own sub-passage or recess, this can form a deadspace where $CO_2$ concentration may not be an accurate reflection of that exhaled (or inhaled) by the infant 1.

The elongate breath indicator 14, 54 is also advantageous because it can be inserted through the duckbilled valve, firstly allowing the therapy to continue as the indicator is inserted in or removed from the manifold, and secondly because the indicator sensing end 15 or sampling end 51 can be pushed to a point where it is closest to the exhaled gases from the infant 1, therefore providing or sampling gas exhaled by the patient for providing an as accurate a reading as possible.

The volume of air exhaled by an infant (tidal volume) is generally very small generally in the range of 1 to 40 milliliters (larger for adults). Accordingly, it is preferred that the indicator is capable of measuring and detecting $CO_2$ in such small tidal volumes. The sensing end 15 or sensor 55 of indicators 14, 54 is advantageous because it can measure small tidal volumes. Further, providing the indicator 14, 54 with sensing end 15 or sampling end 51 to extend close to the infant allows the indicator to measure or sense from sampled gases small tidal volumes from the patient.

As part of an exhalation of gases from a patient, the exhaled gas stream may travel back into the manifold 3. The exhaled gases become diluted as they travel through the manifold 3. The exhaled gases are diluted by the therapy gases received by the manifold through the inlet port 8. The sensing end 15 or sampling end 51 may be about 2 mm to about 8 mm away from the gases outlet allows the sensing end 15 to be exposed to the highest concentration of exhaled gases, or in the case of sampling end 51 directing the gas to sensor 55 of indicator 54, that is before the exhaled gases become too diluted by the therapy gases. This is advantageous because it allows for an accurate representation of a patient's (e.g. infant's) breathing. The $CO_2$ detecting material is adapted to detect very low tidal volumes of $CO_2$. This makes the indicator 14, 54 advantageous since the indicator can detect very low tidal volumes.

The indicator embodiment shown in FIGS. 5 and 6 is advantageous because the exhaled gases are sucked into the indicator tube body due to either the venturi effect or Bernoulli Effect. This is advantageous because the suction allows a substantial part of the exhaled gases to be passed over the $CO_2$ detecting material. This suction of exhaled gases allows the indicator to be more accurate since a substantial part of the exhaled gases passes over the $CO_2$ detecting material without getting diluted by the incoming therapy gases.

The indicator 14 being an elongate shape is advantageous because it does not increase the resistance to the flow of gases in the manifold. The elongate shaped indicator 14 also reduces the resistance to the flow of gases from the inlet port 8 to the gases outlet 9. Preferably the outer surfaces which are exposed to gases flow are smooth to not increase the resistance to gases flow. The apertures 30 in the indicator 14 as shown in FIG. 6 also contribute to reducing the resistance to flow. The apertures 30 allow gases to flow through the indicator as gases flow from the inlet port 8 to the PEEP outlet 10. In addition to this the indicator 14 being an elongate shape as shown in FIG. 3 reduces the dead space of the gas manifold increasing the sensitivity of CO2 measurement detection.

In a further form the breath indicator 14, 54 and breathing apparatus 3 may be sold or packaged or be in the arrangement of a kit of parts. The breath indicator 14, 54 and breathing apparatus 3 have been described above in detail. The kit may be in any suitable form. Preferably instructions of assembling, using and maintaining the breath indicator 14, 54 and breathing apparatus 3 will be supplied with the kit. In use the breath indicator 14, 54 is inserted into the breathing assistance apparatus 3 through a device inlet 12, the device inlet 12 including a duck billed valve. The breath indicator 14, 54 can be locked in place by an optional locking feature, but preferably, the indicator 14, 54 is held in place by friction forces with a duck billed valve, or other port of a patient interface (such as a mask) or T-piece.

Further Embodiment

As discussed above, features of use, detector material or sensor may be applicable to the embodiment described in more detail below.

In a further embodiment, there is provided a breath indicator 54 that is receivable by a part of a breathing assistance apparatus (or patient interface), such a breathing apparatus capable of supplying gas to a patient. It will be appreciated a breathing apparatus may include a ventilator system or resuscitator system, or parts of these, such as T-piece 3.

Such a breath indicator 54 comprises an elongate body 50 having a gas sampling end 51, and an attachment end 56. The attachment end 56 adapted to attach to a part of a breathing assistance apparatus (e.g. via a duck-billed valve of a T-piece) and for locating the gas sampling end 51. The gas sampling end 51 to be located, or for location, at or in, a region where gas from the patient is to be exhaled. Such a gas sampling end 51 being in communication with a sensor (not shown, but to be located at 55) comprising a detector material. The detector material is changeable between a first visual indicator state (relating to an inhalation phase of the patient), and a second visual indicator state (relating to an exhalation phase of the patient). The detector material also being is capable of changing between the visual indicator states at a sufficient rate to substantially correspond with the inhalation and exhalation phases of the patient connected to the breathing assistance apparatus.

As discussed generally in relation to the previous embodiments, the sensor comprises CO2 detecting material. The detecting material used is that which is capable of changing from a first visual indicator state (e.g. first or base colour) to a second indicator state (e.g. second or indicator colour) when exposed to gas having CO2 concentration greater than that normally found in atmospheric air. Similarly, the detecting material is capable of changing from the second visual indicator state to the first indicator state when exposed to gas having CO2 concentration the same or substantially similar to those normally found in atmospheric air. The material chosen is advantageously that which changes from the first visual indicator state to the second visual indicator state when exposed to gas having a concentration by volume of at least about 5% or more CO2.

Advantageously, in this embodiment of the breath indicator 54, the visual indicator state of the detecting material can be optically or visually observed by a user of a breathing assistance apparatus (e.g. ventilator or resuscitator system) for a patient. One other particular use of such a breath indicator is the ability for a user to detect the end-tidal or breath-by-breath CO2 present within gas being exhaled by the patient. Such detection is enabled by the user optically or visually observing the change in visual indictor state of the detecting material.

In various but preferred forms, at least a part of the attachment end 56 of the breath indicator remains external of a part of a breathing assistance apparatus (e.g. patient interface such as a T-piece or mask) to which the breath indicator 54 is attached.

The attachment end 56 can be provided in a substantially perpendicular orientation to the elongate body, and may for example be disk-shaped, such as that shown in FIGS. 10-13.

It should be further appreciated that the attachment end 56 can be formed to be, or so used as, a handle portion including a handle flange extending outwards perpendicularly from the end of the attachment end 56. This may enable a user to better grip or hold the breath indicator 54 when removing the indicator 54 from a patient interface or when inserting the indicator 54 into an interface (or part of a breathing assistance apparatus).

Further, the breath indicator 54 may further comprise of a stopping flange (not shown, but could be similar to that of FIGS. 3-6) that is located at least partway along the elongate body 50 and which extends substantially or generally perpendicularly from the body 50. Such a flange 57 can be located between the attachment end 56 and the sampling end 51.

In a similar manner to the embodiments previously discussed, the exterior surface of the elongate body 50 may be substantially smooth, or otherwise shaped, such that, in-use the elongate body 50 does not increase the resistance to flow of gas through the breathing assistance apparatus to which the indicator 54 is attached.

The elongate body 50 is provided such that it has a length sufficient to allow the gas sampling end 51 to be located in a region where gas from the patient is to be exhaled, and where the attachment end 56 is located in a position attached to a part of a breathing assistance apparatus.

In one example, the elongate body 50 may have an outer diameter of about 1 mm to about 5 mm, and a length of about 30 mm to about 60 mm. It will be appreciated different lengths or elongate body diameter may be used depending on the application and size of breathing apparatus or interface (or patient).

The gas sampling end 51 of the elongate body comprises a gas inlet 52, the inlet 52 being provided for fluid communication with the sensor via a passageway 53. The sensor comprising the detecting material is advantageously provided in-line with the passageway 53, such that the gas flowing through the passageway 53 contacts the sensor (with detecting material) for providing the visual indication of change in gas components (e.g. with respect to CO2). Accordingly, the passageway 53 is provided for extending from the gas sampling end 51 of the elongate body 50 to the sensor.

In more detail, the passageway 53 provides for a gas flow path D extending from the gas inlet 52 to one or more gas outlets 59. Such outlets 59 are provided to be in fluid communication with the surrounding atmosphere external of the resuscitation system. That is, the outlets 59 are provided for allowing the expelling of gas flowing through the passageway 53 to the surrounding environment outside of the breathing apparatus, such as flow path E.

Therefore, the sensor is positionable for contact with the gas flow path D through the passageway 53 is in contact with gases exhaled by a patient when, in a first mode of use such gases flow in through the gas inlet 52 of the sampling end 51, through the passageway 53 and make contact with the sensor. In this mode, a change in the sensor's detector material from the first visual indicator state to the second indicator state (if the CO2 concentration is sufficient) may be enabled. And, in a second mode of use, such as when a patient is in an inhalation phase, gas flow passing through the patient interface enters the gas inlet 52 at the sampling end 51, flows through the passageway 53, and makes contact with the sensor. In such a second mode, the flow of gases being detected by the detecting material allows the change from the second visual indicator state to the first visual indicator state. Such a second mode flushes gases provided to the patient interface or breathing assistance apparatus through the breath indicator 54.

In one configuration, the sensor with detecting material is located in a region adjacent the attachment end 56. In this setup, the attachment end 56, or at least a part of the attachment end 56, is formed of a visually transparent material allowing a user to visually detect changes between the first and second visual indicator states of the detector material (i.e. between the two modes of use and for monitoring the inhalation and exhalation phases of a patient). For example, the top surface 61 of the attachment end 56 may be suitable optical transparency.

Accordingly, the attachment end 56 is enabled with a housing or hollow section 60 for holding or retaining the sensor in position, such that the sensor is in contact with the gas flow path of gas flowing through the passageway 53 prior to being expelled to the external environment out of the gas outlets 59. The housing 60 or attachment end 56 (or parts of each) may be of visually transparent materials enabling a user to observe the changes between the visual indicator states of the detecting material.

As discussed previously, the breath indicator 54 as described above may be utilised together with a T-piece, or patient interface. In such an arrangement, the manifold of the T-piece, when in function, has higher pressure than the atmosphere, hence a pressure difference is created between the sampling end 51 and gas outlets 59. The pressure difference helps to direct the exhaled gases towards the detecting material at the attachment end 56.

Figure 7:
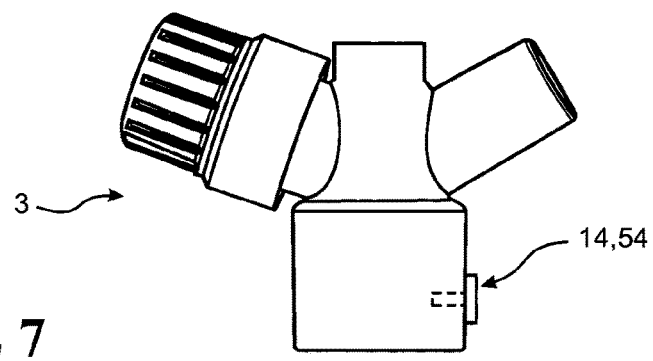
FIGS. 7, 8 and 9 show alternative arrangements where the breath indicator may be attached to, or received by, a T-piece apparatus or a patient interface, such as a face mask, such an indicator may be that of FIG. 3-6 or 11-13.
Figure 8:
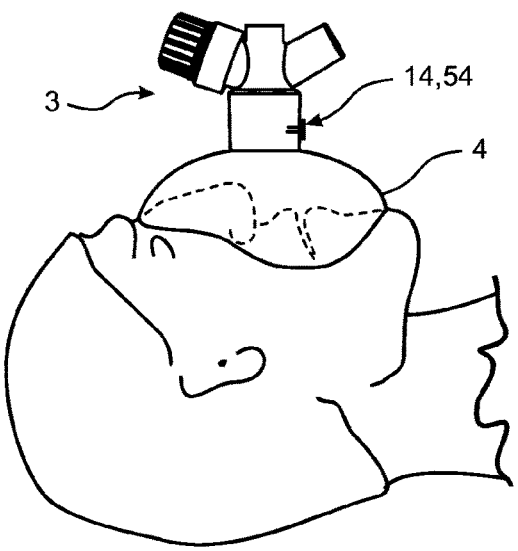
Figure 9:
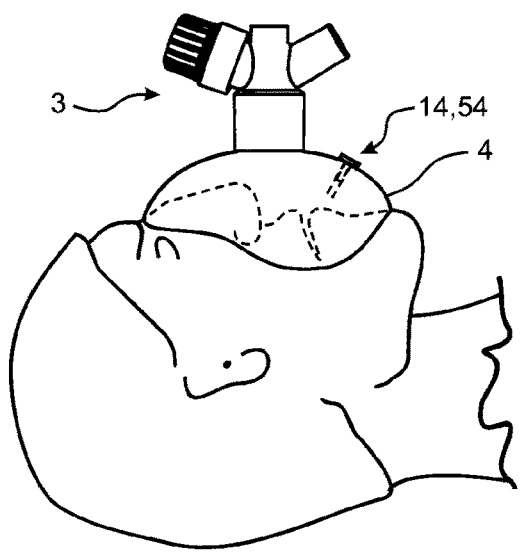

It should also be appreciated that the breath indicator 14 or 54, may be utilised directly with a face mask or other such patient interface, or may be positioned for receipt by a component of a breathing assistance apparatus, such as a T-piece, as shown by FIGS. 7, 8, 9. The breath indicators 14, 54 of this invention provide for a removable indicator that may be received or attached to a part of a breathing assistance apparatus, with a system for placing the sensor close to the region of patient where gases are being exhaled, or alternatively where a sampling end or collector is provided for directing exhaled gas from a patient to a sensor for providing an indication of exhaled gas components (e.g. CO2).

The present invention may have particular application to an infant or neonate due to the ability to locate a sensor or sampling end for sampling of gases close to the point or region of exhalation by an infant or neonate. Infants and neonates have a particular problem in that their volume of exhaled breath is comparatively small compared to an adult, accordingly, if an indication of exhalation of a patient is to be made for an infant or neonate, it is useful that what breath is exhaled is sensed by a breath indicator.

The invention claimed is:

1. A breath indicator receivable by a device inlet of a breathing assistance apparatus that supplies gas to a patient, the indicator comprising:
   an elongate body having a gas sampling end and an attachment end,
   the attachment end adapted to attach to a part of the breathing assistance apparatus to position the gas sampling end in a location within a manifold of the breathing apparatus,
   the gas sampling end including a sensor, the sensor comprising a detector material changeable between a first visual indicator state relating to an inhalation phase of the patient and a second visual indicator state relating to an exhalation phase of the patient,
   wherein the breath indicator is removably insertable into the device inlet while the breathing assistance apparatus supplies gas to the patient, and
   wherein the detector material changes between the first and second visual indicator states at a sufficient rate to substantially correspond with the inhalation and exhalation phases of the patient.

2. The breath indicator as claimed in claim 1, wherein the detecting material is $CO_2$ detecting material.

3. The breath indicator as claimed in claim 1, wherein the detecting material changes from the first visual indicator state to the second indicator state when exposed to gas having a $CO_2$ concentration greater than that normally found in atmospheric air.

4. The breath indicator as claimed in claim 1, wherein the detecting material changes from the second visual indicator state to the first indicator state when exposed to gas having a $CO_2$ concentration the same or substantially similar to that normally found in atmospheric air.

5. The breath indicator as claimed in claim 1, wherein the detecting material changes from the first visual indicator state to the second visual indicator state when exposed to gas having a concentration by volume of at least about 5% $CO_2$.

6. The breath indicator as claimed in claim 1, wherein in use, end-tidal or breath-by-breath $CO_2$ present within gas exhaled by the patient is optically or visually observable by change in visual indictor state of the detecting material.

7. The breath indicator as claimed in claim 1, wherein at least a part of the attachment end remains external of a part of the breathing assistance apparatus to which the breath indicator is attached.

8. The breath indicator as claimed in claim 7, wherein the attachment end is provided substantially perpendicular to the elongate body and the elongate body is longer than the attachment end is wide.

9. The breath indicator as claimed in claim 7, wherein the attachment end is formed as a handle portion including a handle flange extending outwards perpendicularly from the end of the elongate body.

10. The breath indicator as claimed in claim 1, wherein said breath indicator further comprises a stopping flange located partway along said elongate body and extending substantially perpendicularly from said elongate body, said flange being located between said attachment end and said gas sampling end.

11. The breath indicator as claimed in claim 1, wherein the breath indicator is receivable by a patient interface.

12. The breath indicator of claim 11, wherein the patient interface comprises one or more of a face mark, an oral mask, an oronasal mask, a nasal mask, one or a pair of nasal prongs, an endotracheal tube, or a T-piece resuscitator apparatus.

13. The breath indicator as claimed in claim 1, wherein an exterior surface of the elongate body is substantially smooth such that the elongate body is adapted to not substantially increase a resistance to flow of gas through a part of a breathing assistance apparatus to which the indicator is attached.

14. The breath indicator as claimed in claim 1, wherein the gas sampling end of the elongate body comprises a gas inlet, the gas inlet being in fluid communication with the sensor via a passageway.

15. The breath indicator as claimed in claim 14, wherein the sensor comprising the detecting material is provided in-line with the passageway.

16. The breath indicator as claimed in claim 1, wherein at least a portion of a manifold wall and at least a portion of the gas sampling end are configured to allow a user to view changes between the first and second visual indicator states of the detector material.

17. The breath indicator of claim 1, further comprising an alignment feature configured to position the elongate body in a position that locates the gas sampling end closer to where exhaled gases are received into the breathing assistance apparatus than the attachment end.

18. The breath indicator of claim 1, wherein the gas sampling end is positioned in a flow pathway where gas from the patient is inhaled and exhaled.

* * * * *

UNITED STATES PATENT AND TRADEMARK OFFICE
CERTIFICATE OF CORRECTION

| | | |
|---|---|---|
| PATENT NO. | : 10,149,953 B2 | Page 1 of 1 |
| APPLICATION NO. | : 13/820018 | |
| DATED | : December 11, 2018 | |
| INVENTOR(S) | : Church et al. | |

It is certified that error appears in the above-identified patent and that said Letters Patent is hereby corrected as shown below:

In the Specification

In Column 5 at Line 22, change "indicator" to --indicator.--.

In Column 6 at Line 47, change "use" to --use.--.

In Column 7 at Line 39, change "indicator" to --indicator.--.

In Column 9 at Line 64, change "FIG." to --FIGS.--.

In the Claims

In Column 24 at Line 64, in Claim 12, change "face mark," to --face mask,--.

Signed and Sealed this
Twenty-first Day of May, 2019

Andrei Iancu
*Director of the United States Patent and Trademark Office*